United States Patent
Andersson et al.

(10) Patent No.: US 11,723,570 B2
(45) Date of Patent: *Aug. 15, 2023

(54) IDENTIFYING SENSORY INPUTS AFFECTING WORKING MEMORY LOAD OF AN INDIVIDUAL

(71) Applicant: Telefonaktiebolaget LM Ericsson (publ), Stockholm (SE)

(72) Inventors: Lars Andersson, Solna (SE); Matthew John Lawrenson, Bussigny (CH)

(73) Assignee: TELEFONAKTIEBOLAGET LM ERICSSON (PUBL), Stockholm (SE)

(*) Notice: Subject to any disclaimer, the term of this patent is extended or adjusted under 35 U.S.C. 154(b) by 0 days.

This patent is subject to a terminal disclaimer.

(21) Appl. No.: 17/668,607

(22) Filed: Feb. 10, 2022

(65) Prior Publication Data

US 2022/0265186 A1 Aug. 25, 2022

Related U.S. Application Data

(63) Continuation of application No. 16/345,106, filed as application No. PCT/EP2016/075748 on Oct. 26, 2016, now Pat. No. 11,259,730.

(51) Int. Cl.
*A61B 5/16* (2006.01)
*A61B 5/00* (2006.01)
(Continued)

(52) U.S. Cl.
CPC .............. *A61B 5/168* (2013.01); *A61B 3/112* (2013.01); *A61B 5/0036* (2018.08);
(Continued)

(58) Field of Classification Search
CPC ........ A61B 5/168; A61B 3/112; A61B 5/0036; A61B 5/0077; A61B 5/0205; A61B 5/165;
(Continued)

(56) References Cited

U.S. PATENT DOCUMENTS 6,434,419 B1 * 8/2002 Gevins .................. G16H 50/20
600/544
9,265,458 B2 2/2016 Stack
(Continued)

FOREIGN PATENT DOCUMENTS

CN 101690666 A 4/2010
CN 102727223 A 10/2012
(Continued)

OTHER PUBLICATIONS

Search Report issued in Russian Application No. 2019116015 (dated Oct. 29, 2019).
(Continued)

*Primary Examiner* — Ryan W Sherwin
(74) *Attorney, Agent, or Firm* — Rothwell, Figg, Ernst & Manbeck, P.C.

(57) ABSTRACT

In an aspect of the invention, a method of identifying sensory inputs affecting working memory load of an individual is provided. The method comprises monitoring (S101) working memory load of the individual using a sensor device, detecting (S102) an increase in the working memory load of the individual, and identifying (S103), in response to the detected increase, at least one sensory input affecting the working memory load of the individual.

26 Claims, 6 Drawing Sheets

(51) Int. Cl.
*A61B 5/0205* (2006.01)
*A61B 3/11* (2006.01)
*A61B 5/38* (2021.01)
*A61B 5/318* (2021.01)
*A61B 5/378* (2021.01)
*A61B 5/381* (2021.01)
*A61B 5/024* (2006.01)
*A61B 5/107* (2006.01)
*A61B 5/02* (2006.01)
*A61B 5/24* (2021.01)
*A61B 5/369* (2021.01)

(52) U.S. Cl.
CPC .......... *A61B 5/0077* (2013.01); *A61B 5/0205* (2013.01); *A61B 5/165* (2013.01); *A61B 5/318* (2021.01); *A61B 5/378* (2021.01); *A61B 5/38* (2021.01); *A61B 5/381* (2021.01); *A61B 5/4005* (2013.01); *A61B 5/02* (2013.01); *A61B 5/024* (2013.01); *A61B 5/1079* (2013.01); *A61B 5/24* (2021.01); *A61B 5/369* (2021.01); *A61B 5/4088* (2013.01); *A61B 5/6897* (2013.01); *A61B 2503/24* (2013.01)

(58) Field of Classification Search
CPC .......... A61B 5/318; A61B 5/378; A61B 5/38; A61B 5/381; A61B 5/4005; A61B 5/02; A61B 5/024; A61B 5/1079; A61B 5/24; A61B 5/369; A61B 5/4088; A61B 5/6897; A61B 2503/24; A61B 5/163; A61B 5/4836; A61B 5/00; G06N 5/02
See application file for complete search history.

(56) References Cited

U.S. PATENT DOCUMENTS

| | | | |
|---|---|---|---|
| 9,711,056 | B1 | 7/2017 | Nguyen |
| 10,827,926 | B2 | 11/2020 | Blackwell et al. |
| 2003/0013981 | A1 | 1/2003 | Gevins et al. |
| 2004/0193068 | A1* | 9/2004 | Burton .................. A61B 5/369 600/595 |
| 2007/0165019 | A1 | 7/2007 | Hale et al. |
| 2007/0225577 | A1 | 9/2007 | Mathan |
| 2007/0236488 | A1 | 10/2007 | Mathan et al. |
| 2009/0164132 | A1 | 6/2009 | Jung et al. |
| 2009/0312665 | A1 | 12/2009 | Daimoto et al. |
| 2010/0092929 | A1 | 4/2010 | Hallowell et al. |
| 2010/0185113 | A1 | 7/2010 | Peot et al. |
| 2010/0250322 | A1 | 9/2010 | Norwood et al. |
| 2010/0292545 | A1 | 11/2010 | Berka et al. |
| 2010/0331661 | A1* | 12/2010 | Nakagawa ............. A61B 5/369 600/386 |
| 2011/0105859 | A1 | 5/2011 | Popovic et al. |
| 2011/0218953 | A1 | 9/2011 | Hale et al. |
| 2012/0209798 | A1 | 8/2012 | Kaushal et al. |
| 2013/0131438 | A1 | 5/2013 | Brewer et al. |
| 2014/0139551 | A1 | 5/2014 | McCulloch et al. |
| 2014/0186806 | A1* | 7/2014 | Hallowell .............. G09B 19/04 434/167 |
| 2014/0272839 | A1 | 9/2014 | Cutler |
| 2015/0066104 | A1 | 3/2015 | Wingeier et al. |
| 2015/0351655 | A1 | 12/2015 | Coleman |
| 2016/0022136 | A1 | 1/2016 | Ettenhofer et al. |
| 2017/0035317 | A1 | 2/2017 | Jung et al. |
| 2017/0123028 | A1 | 5/2017 | Hammer et al. |
| 2017/0229037 | A1 | 8/2017 | Gazzaley et al. |
| 2018/0075772 | A1* | 3/2018 | Carr ..................... G09B 19/00 |
| 2018/0146910 | A1 | 5/2018 | De Vries et al. |
| 2019/0384392 | A1 | 12/2019 | Aimone et al. |

FOREIGN PATENT DOCUMENTS

| | | |
|---|---|---|
| CN | 103239227 A | 8/2013 |
| CN | 104777977 A | 7/2015 |
| CN | 108703762 A | 10/2018 |
| JP | 2008092365 A | 4/2008 |
| KR | 2002-0066445 A | 8/2002 |
| RU | 61899 U1 | 3/2007 |
| RU | 2428927 C2 | 5/2011 |
| RU | 165429 U1 | 10/2016 |
| WO | 2015164807 A1 | 10/2015 |
| WO | 2016/198030 A1 | 12/2016 |

OTHER PUBLICATIONS

Shewchuk, Darrin, "HARMAN Demonstrates Industry's First Pupil-Based Driver Monitoring System at CES 2016", Automotive, Jan. 5, 2016 (3 pages).

International Search Report and Written Opinion dated Jun. 23, 2017 issued in International Application No. PCT/EP2016/075748. (9 pages).

Nierhaus, T. et al., "Background and evoked activity and their interaction in the human brain", Magnetic Resonance Imaging 27 (2009) 1140-1150. (11 pages).

Ross V. et al., "Investigating the influence of working memory capacity when driving behavior is combined with cognitive load: An LCT study of young novice drivers", Accident Analysis and Prevention 62 (2014) 377-387. (11 pages).

Wilsch, A. et al., "What works in auditory working memory? A neural oscillations perspective", Brain Research 1640 (2016) 193-207. (15 pages).

Klingner, J. et al., "Measuring the Task-Evoked Pupillary Response with a Remote Eye Tracker", Stanford University, (Mar. 2008). (4 pages).

Zahran, R. et al., "Evaluating Pupil Dilation as a Measure of Working Memory and Logical Thinking Manuscript", (Sep. 2015). Student Summer Scholars. Paper 155. http://scholarworks.gvsu.edu/sss/155. (11 pages).

* cited by examiner

IDENTIFYING SENSORY INPUTS AFFECTING WORKING MEMORY LOAD OF AN INDIVIDUAL

CROSS-REFERENCE TO RELATED APPLICATIONS

This application is a continuation of U.S. application Ser. No. 16/345,106, filed on Apr. 25, 2019 (status pending), which is a 35 U.S.C. § 371 National Stage of International Patent Application No. PCT/EP2016/075748, filed Oct. 26, 2016. The above identified applications are incorporated by this reference.

TECHNICAL FIELD

The invention relates to a method of identifying sensory inputs affecting working memory load of an individual, a device for identifying sensory inputs affecting working memory load of an individual, a corresponding computer program, and a corresponding computer program product.

BACKGROUND

Concentration makes people less susceptible to distraction, but involves considerable cognitive straining. The extent to which people can focus on a certain task depends on the exact nature and difficulty of that task and the modality (e.g., visual, verbal) of the distraction in comparison with the task.

Working memory is the small amount of information in a person's mind that they can readily access. The working memory is used for cognitive tasks such as reasoning and problem solving. The information retained in one's working memory is temporary; it disappears unless it is stored in the long-term memory. Also, the amount of information that can be stored in the working memory is limited. Competing sensory inputs (i.e., distractions) can result in high working memory load, which can limit one's cognitive capabilities. Measurement of pupil diameter can be used to obtain information about demand for working memory in different cognitive activities.

Cognitive load can be exemplified by measuring pupillary response as a person is undergoing various mental processes. Studies show the mental effort required to perform a calculation, and how this effort changes throughout the process of the task.

For instance, a study has been performed that attempted to correlate different pupil measurements, namely fixation duration and pupil size, with memory load and processing load. The study discovered that the increase in fixation duration with number of targets both within and above working memory capacity suggests that in free viewing, fixation duration is sensitive to actual memory load as well as to processing load, whereas pupil size is indicative of processing load only. Hence, it was concluded that fixation duration is selective to memory load for targets. In contrast, changes in pupil size are too slow for isolating instances of memory accumulation such as target encoding in the free viewing search task. Pupil size most likely reflects an overall processing load which incorporates several cognitive processes.

The effect that the performing of tasks has on the human pupil is called 'task-evoked pupillary response'. Recent work, for instance "Measuring the Task-Evoked Pupillary Response with a Remote Eye Tracker" by J. Klingner, R. Kumar, and P. Hanrahan, in Proceedings of the 2008 symposium on Eye tracking research & applications (ETRA '08), pages 69-72, ACM New York, 2008, has found that remote video eye trackers have enough precision to be used for detailed task-evoked pupillary measurements.

An electroencephalogram (EEG) is a technique whereby electrical signals on the scalp, forehead or in-ear regions are measured for determining brain activity. In the literature it has been shown that EEG measurements can be linked to cognitive tasks. For instance, the measuring of EEG signals can be used to classify a mental task with relatively high accuracy. As an example, mentally letter writing, in which subjects were instructed to mentally compose a letter to a friend without vocalizing, could be distinguished from the task of mentally multiplying two multi-digit numbers, such as 49 times 78.

A number of devices and associated methods are available to gather knowledge of what sensory inputs are in the local area of a subject or user, i.e., what is nearby that could be sensed by the user. Some examples are given in the following.

Imaging sensors can be used to identify objects within the field of view of the sensors. The use of image sensors in object recognition has become particularly powerful due to the development of machine-learning algorithms which can identify objects in images or video with a high degree of accuracy.

Lightfield cameras are able to capture data about the lightfield emanating from a scene. As such more data can be obtained than if just a single plane is recorded, as per a standard camera. As such 3D images can be obtained using a single camera with a single lens.

Sensors based on LIDAR ("Light Detection And Ranging") are able to scan their environment to gain a 3D map of their environment, and thus provide data to an algorithm that can identify objects. Recently 'on chip' implementations or LIDAR has been prototyped, providing a path to low cost implementations as low as $10. RADAR ("Radio Detection And Ranging") also has the capability to identify objects.

Audio sensors, i.e., microphones, can also be used to identify different events. Algorithms have been developed for identifying events based on the sounds they produce. When combined with directional microphones this allows a user to associate an action (event) and location with an event.

Devices that are able to identify smell (so called electronic noses) have been developed. While these vary greatly in terms of the underlying technology some extremely powerful devices are now available at mass market prices, and in fact have been incorporated into devices such as those to detect use of alcohol or marijuana.

A number of devices and associated methods are available to obscure sensory inputs from a user—i.e., either mask or remove a sensory input such that it is no longer noticed by the user. Some examples are given in the following.

Augmented Reality (AR) is a technology which allows to change how the physical environment appears to the user, by artificially adding computer generated content that blends with the environment. This can be visual content, e.g., using AR headsets. AR has potential in entertainment (media, gaming) but also in education and for professional use.

Recently a number of 'active hearing' devices have been released to the market or announced. Examples include, the 'Here One' from Doppler Labs and the 'Pilot' from Waverly Labs. Whilst the Pilot demonstrates the ability to add intelligence to hearing devices (purportedly it will translate between users speaking different languages), the Here One modifies the level to which various sounds are either heard or not heard.

Devices that are able to synthesise odour are available in the market or have been announced, an example being the 'Cyrano'. Other groups have worked on screens that can project smells by using fans to locate a smell on a certain part of a screen. Odour can be masked by another odour where a first smell is replaced by a stronger second smell, or it can masked by using white odour. Scientists discovered that similarly to white light, where the combination of many wavelengths produce white (seemingly colourless) light, mixtures with many odour components can produce a smell that is difficult to distinguish.

Content filtering is a way of altering or restricting digital content, such as advertisement, inappropriate material, or potentially hostile applications. Content filtering software is used for different reasons, one of which can be the blocking of unwanted distractions while browsing the Internet. The use of AR offers the possibility of "real world" ad blocking, which is the blocking of e.g., brand logos and advertisements in the physical environment of the AR device user.

Productivity apps are computer programs that help increased productivity and improve concentration and focus, e.g., by filtering or blocking of distracting content, by setting timers, or by scheduling work and breaks taking into account the user's attention span.

However, existing solutions have problems.

As regards identification and removal of potentially distracting sensory inputs: working memory load: existing solutions require the user to think actively about what is distracting them, being itself detrimental to the working memory load of the user; universality: existing solutions only target certain types of distracters (e.g., block website advertisements) or focus on just one of the user's sensory inputs (e.g., only block audio inputs).

As regards feedback/control: (1) focus detection: existing solutions do not directly measure the actual working memory load of the user, and thus have less information about the need for the removal of distracters and what distracters should be removed; (2) effect of removal: existing solutions do not directly measure the effectiveness of the removal of individual distracters on the user's working memory load.

SUMMARY

An object of the present invention is to solve or, at least mitigate, the problem in the art of how to provide method of identifying sensory inputs affecting working memory load of an individual.

This object is attained in a first aspect of the invention by a method of identifying sensory inputs affecting working memory load of an individual. The method comprises monitoring working memory load of the individual using a sensor device, detecting an increase in the working memory load of the individual and identifying, in response to the detected increase, at least one sensory input affecting the working memory load of the individual This object is attained in a second aspect of the invention by a device for identifying sensory inputs affecting working memory load of an individual. The device comprises a sensor device configured to monitor working memory load of the individual, and a processing unit configured to detect an increase in the working memory load of the individual and to identify, in response to detecting the increase, at least one sensory input affecting the working memory load of the individual.

Hence, a sensor device is used to monitor working memory load of an individual. In an example, the individual is seated in front of her computer and a built-in camera of the computer is used as a sensor device for monitoring the working memory load by monitoring one or both eyes of the individual.

The example camera may further be used in combination with a processing unit of the computer for detecting any increase in the working memory load of the individual. For instance, the processing unit may, during the monitoring by the camera of the individual, detect a change in working memory load in the form of, e.g., a sudden increase in pupil size of one or both eyes of the individual. Such detection indicates an increase in working memory load of the individual.

Upon such detection, the processing unit of the computer may identify at least one sensory input affecting the working memory load of the individual. For example, a built-in microphone of the computer is used in combination with the processing unit and registers a sound being likely to be the sensory input causing the detected increase in working memory load.

This identification of sensory inputs affecting the working memory load of the individual is highly advantageous and can, as will be discussed in various embodiments in the following, be used for many purposes.

In an embodiment of the invention, after having identified at least one sensory input affecting the working memory load of the individual, the processing unit is configured to diminish an impact that the identified at least one sensory input has on the working memory load of the individual.

For instance, if the individual resides in a connected home where many functions such as heating, light and blind control, activation of kitchen equipment etc., are connected to a local area network, such as a Wireless Local Area Network (WLAN), along with any computers, tablets, smart phones, etc, actions may be initiated to mitigate the negative effect which the sensory inputs have on the working memory load of the individual.

Now, if a change in working memory load is monitored and detected by a camera and processing unit of a tablet or smartphone currently operated by the individual, by observing an increased pupil diameter, the processing unit of the individual's tablet may identify—by measuring ambient temperature or communicating with a heat control system—that it is the heating of the home that is set to a too high temperature which negatively affects the working memory load of the individual.

As a result thereof, the processing unit of the tablet transmits a control signal via the WLAN to a home heating control system, i.e., a source of the identified sensory input, to lower the temperature to thereby advantageously diminish an impact that the identified at least one sensory input has on the working memory load of the individual.

It is noted that in this example, a slightly too high indoor temperature would typically not cause a sudden change in the working memory load but a change that must be monitored over an extended period of time.

In another example, the individual wears a pair of headphones equipped with noise-reducing capability, and the camera and processing unit of the tablet that the individual currently is operating detect an increase in pupil size, thereby indicating an increased working memory load of the individual.

The noise-reducing headphones are further equipped with a microphone acting as a sensory input detection device in combination with a processing unit of the headphones for registering disturbing background noise. After receiving a wireless or wired signal from the computer indicating that an increase in working memory load has been detected, the processing unit of the noise-reducing headphones initiates a countermeasure to the identified sensory input by subjecting the individual to a signal which is an out-of-phase representation of the background noise, thereby effectively cancelling out the background noise.

In another embodiment of the invention, the identifying of a sensory input affecting the working memory load of the individual is advantageously performed by identifying a sensory input coinciding in time with the detected increase in the working memory load, wherein the identified at least one sensory input is considered to be the sensory input affecting the working memory load of the individual.

This is advantageous if a sensory input occurs which gives rise to a rather sudden increase in working memory load such as, e.g., when the individual is subjected to a sound or a light having an immediate impact on the working memory load. However, in case the individual is subjected to a less evident sensory input, such as, e.g., a change in temperature which generally is a much slower process, a processing unit acting as a sensory input detection device may have to evaluate events which have happened during a recent period of time, for instance during the last 10 minutes. As an example, the sensory input detection device may be a temperature sensor used in combination with the processing unit for evaluating whether an increase in temperature has occurred over the last 10 minutes, or even a gas sensor evaluating whether a particular chemical substance is present in ambient air.

In another embodiment of the invention, for each identified sensory input, a measure with which the identified at least one sensory input affects the working memory load of the individual is advantageously determined. For instance, the measure may be configured to assume a value between 10 and 100, where 10 would imply a small impact, while 100 would imply a major impact on the working memory load of the individual.

In another embodiment of the invention, the measure associated with a particular sensory input may be stored in a database for later use. In practice, in a situation where the individual is subjected to a plurality of sensory inputs, it may be difficult to assess which particular input(s) affect(s) the individual the most.

In an embodiment of the invention, by utilizing a database comprising a measure associated with each type of sensory input, the processing unit being configured to diminish the impact of the sensory input(s) may conclude by assessing the database that one or a couple of different sensory inputs usually affect the individual to higher degree than others, and accordingly diminishes the effect of these high-impact sensory inputs.

Advantageously, in an embodiment of the invention, it is possible to utilize a learning phase during which the individual purposely is subjected to different sensory inputs while changes in the working memory load of the individual are monitored. Further, a measure associated with each sensory input is estimated and stored in a database for subsequent use.

In the above examples, the change in the individual's work load is detected by means of a processing unit analysing images captured by a camera. However, other sensor devices are envisaged, such as EEG sensors, electrocardiogram (EKG) sensors, heart rate meters, etc.

Further, as has been discussed with reference to what is known in the art in the above, a number of different sensory input detection devices may be envisaged.

Further provided is a computer program comprising computer-executable instructions for causing a device to perform steps of the method according to the first aspect of the invention, when the computer-executable instructions are executed on a processing unit included in the device.

Further provided is a computer program product comprising a computer readable medium, the computer readable medium having the computer program of the device embodied thereon.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

Figure 1:
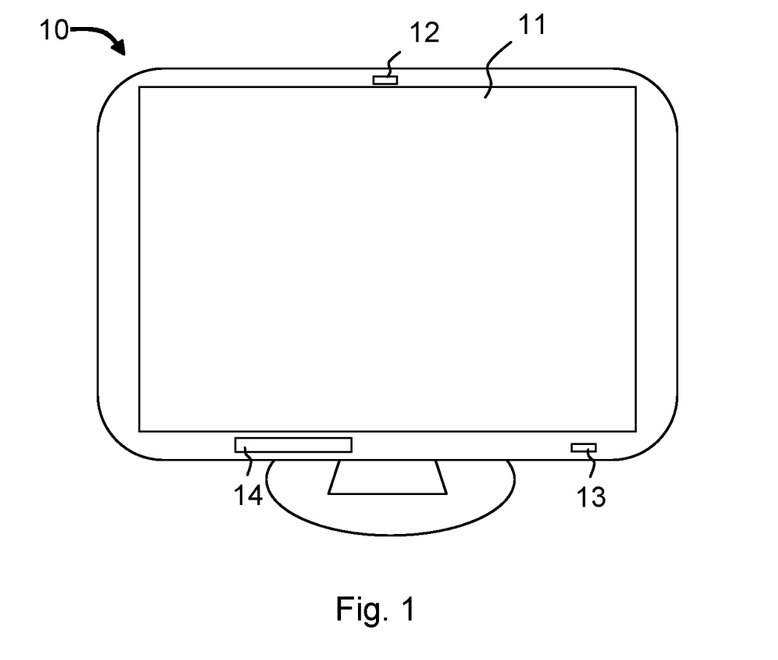
FIG. 1 illustrates a device for identifying sensory inputs affecting working memory load of an individual, according to an embodiment of the invention.

FIG. 1 illustrates a device 10 for identifying sensory inputs affecting working memory load of an individual according to an embodiment of the invention. The device is and shows a device exemplified in the form of a desktop computer 10 in a front view, having a screen 11, a camera 12, a microphone 13, and a loudspeaker 14.

Figure 2:
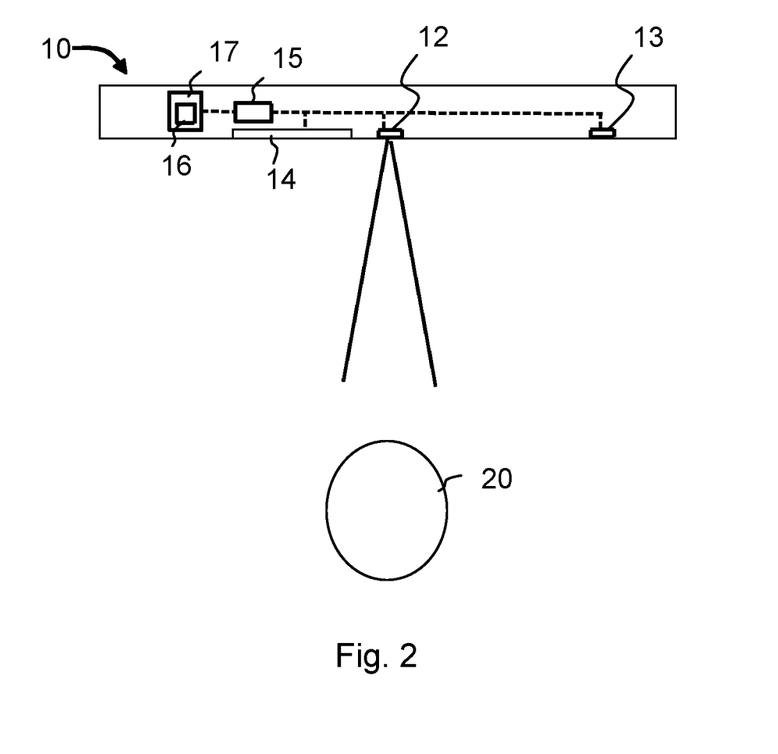
FIG. 2 shows a top view of the device of FIG. 1 with a user seated in front of the device.

FIG. 2 shows a top view of the desktop computer 10, with a user 20 seated in front of it. As can be seen, the camera 12, the microphone 13, and the loudspeaker 14 are operatively coupled to a processing unit 15 embodied in the form of one or more microprocessors arranged to execute a computer program 16 downloaded to a suitable storage medium 17 associated with the microprocessor 15, such as a Random Access Memory (RAM), a Flash memory, a hard disk drive, a cloud service or other information storage devices. The processing unit 15 is arranged to control operation of the desktop computer 10 when the appropriate computer program 16 comprising computer-executable instructions is downloaded to the storage medium 17 and executed by the processing unit 15. The storage medium 17 may also be a computer program product comprising the computer program 16. Alternatively, the computer program 16 may be transferred to the storage medium by means of a suitable computer program product, such as a Digital Versatile Disc (DVD) or a memory stick. As a further alternative, the computer program may be downloaded to the storage medium 17 over a network. The processing unit 15 may alternatively be embodied in the form of a digital signal processor (DSP), an application specific integrated circuit (ASIC), a field-programmable gate array (FPGA), a complex programmable logic device (CPLD), etc.

As discussed hereinbefore, the computer 10 is in an embodiment configured to identify events that have an unwanted effect on the focus of the user, e.g., whilst the user performs a cognitively demanding task.

Figure 3:
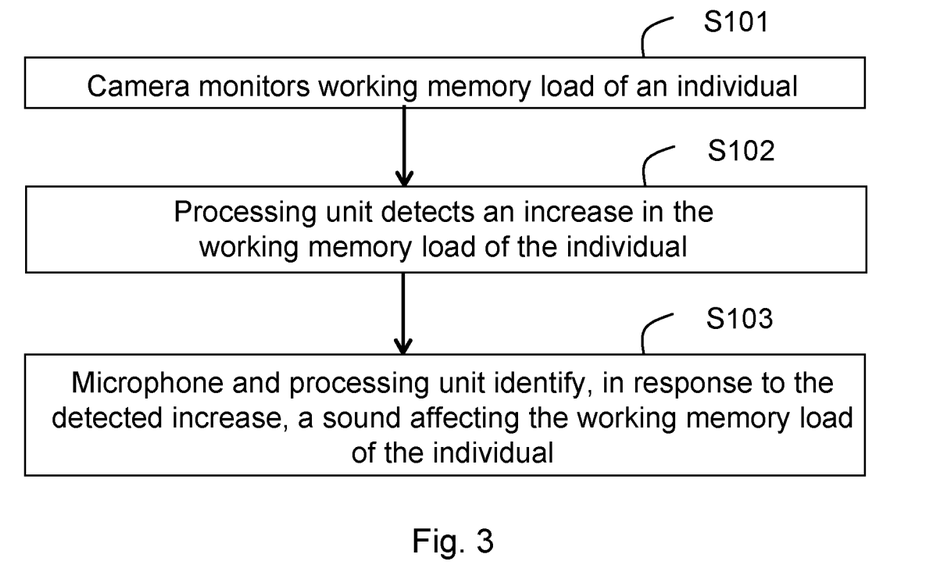
FIG. 3 illustrates a flowchart of a method of identifying sensory inputs affecting working memory load of an individual, according to an embodiment of the invention.

As can be seen in FIG. 2, the user 20 of the computer 10 is, when seated in front of the screen 11, positioned in a field of view of the camera 12. A method of identifying sensory inputs affecting working memory load of an individual—i.e., the user 20—will be described in the following with reference to FIG. 2 and further to FIG. 3 illustrating a flowchart of the method.

A sensor device is used to monitor working memory load of an individual in step S101. In this particular exemplifying embodiment, the sensor device is embodied by the camera 12 which monitors one or both eyes of the user 20. Now, if the user 20 becomes distracted by a sensory input, the working memory load will increase, which typically results in an increase of the pupils of the user's eyes.

In an embodiment of the invention, it is envisaged that if the diameter of the pupil of one of the user's eyes increase above a threshold value, for instance 0.5 mm, the working memory load of the user 20 is considered to have increased. It is further envisaged that different threshold values are used; for example, a 0.2 mm increase represents a first working memory load value A, a 0.4 mm increase represents a second working memory load value B, a 0.6 mm increase represents a third working memory load value C, and so on.

In step S102, the camera 12 (or the processing unit 15 analysing images captured by the camera 12), detects an increase in the working memory load of the user 20, for instance by concluding that the diameter of the pupils of the user's eyes has increased above a certain threshold value.

In response to the detected increase in the user's working memory load, a sensory input detection device—in this particular embodiment being exemplified by the processing unit 15 receiving signals from the microphone 13—advantageously identifies one or more sensory inputs affecting the working memory load of the user 20 in step S103. In this example, the built-in microphone 13 of the computer 20 registers a sound being likely to be the sensory input causing the detected change in working memory load of the user 20.

In an embodiment, the sensory input, in this example being a sound, is advantageously identified by the processing unit 15 to coincide in time with the detected increase in the working memory load, thereby being considered to be the sensory input causing the increase. Thus, if the sound was recorded just before the increase in working memory load was detected, the sound is considered be the sensory input causing the increase.

In an embodiment, upon having identified a sensory input affecting the working memory load of the user 20, actions are taken to diminish the impact that the sensory input has on the working memory load, as will be discussed in the following.

Figure 4:
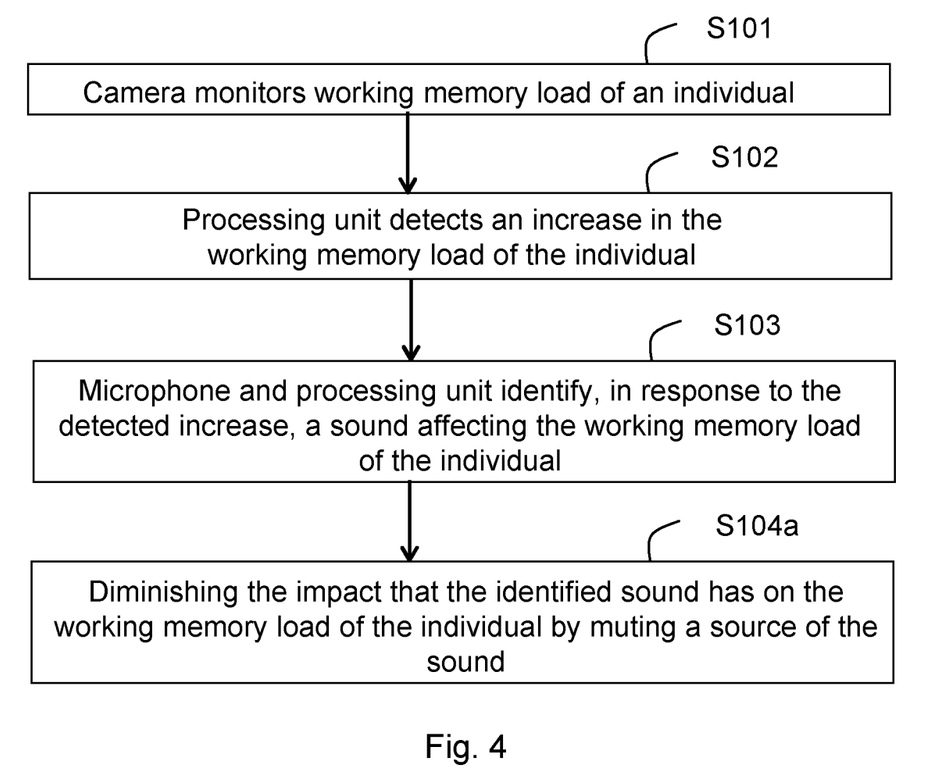
FIG. 4 illustrates a flowchart of a method of identifying sensory inputs affecting working memory load of an individual, according to another embodiment of the invention.

In the embodiment illustrated in the flowchart of FIG. 4, after the microphone 13 has recorded a sound being considered to be the sensory input causing the increase in working memory load in step S103, the processing unit 15 of the computer 10 concludes that the user 20 herself just started an audio player of the computer 10 and advantageously lowers a sound level being output by the audio player via the loudspeaker 14 of the computer 10 in step S104a, since the selected audio level is too high and thus affects the working memory load of the user 20. Hence, in this particular embodiment, the impact that the identified sensory input has on the working memory load of the user is diminished using the processing unit 15 controlling the very source of the identified sensory input, in this case being the computer loudspeaker 14.

In another embodiment illustrated with reference to FIGS. 5 and 6, the impact of the sensory input on the user's working memory load is diminished by initiating a countermeasure to the identified one sensory input.

Figure 5:
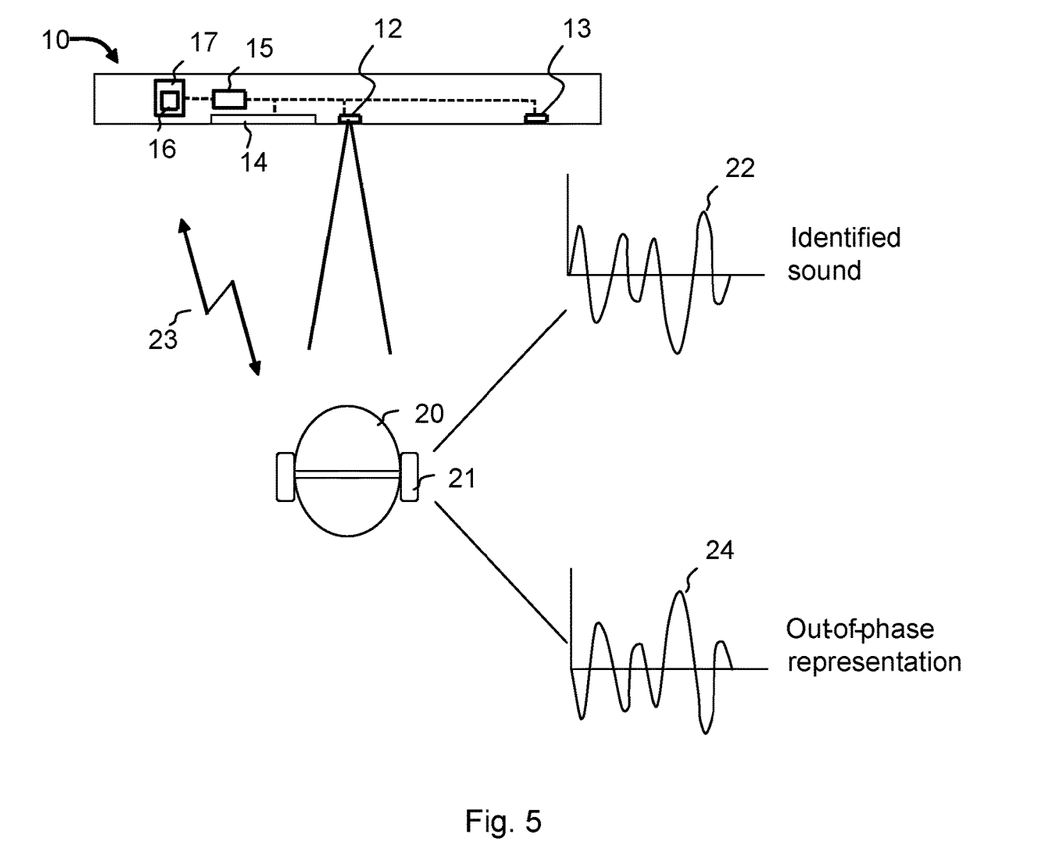
FIG. 5 shows a top view of the device of FIG. 1 with a user seated in front of the device equipped with a pair of headphones with noise-reducing capability.
Figure 6:
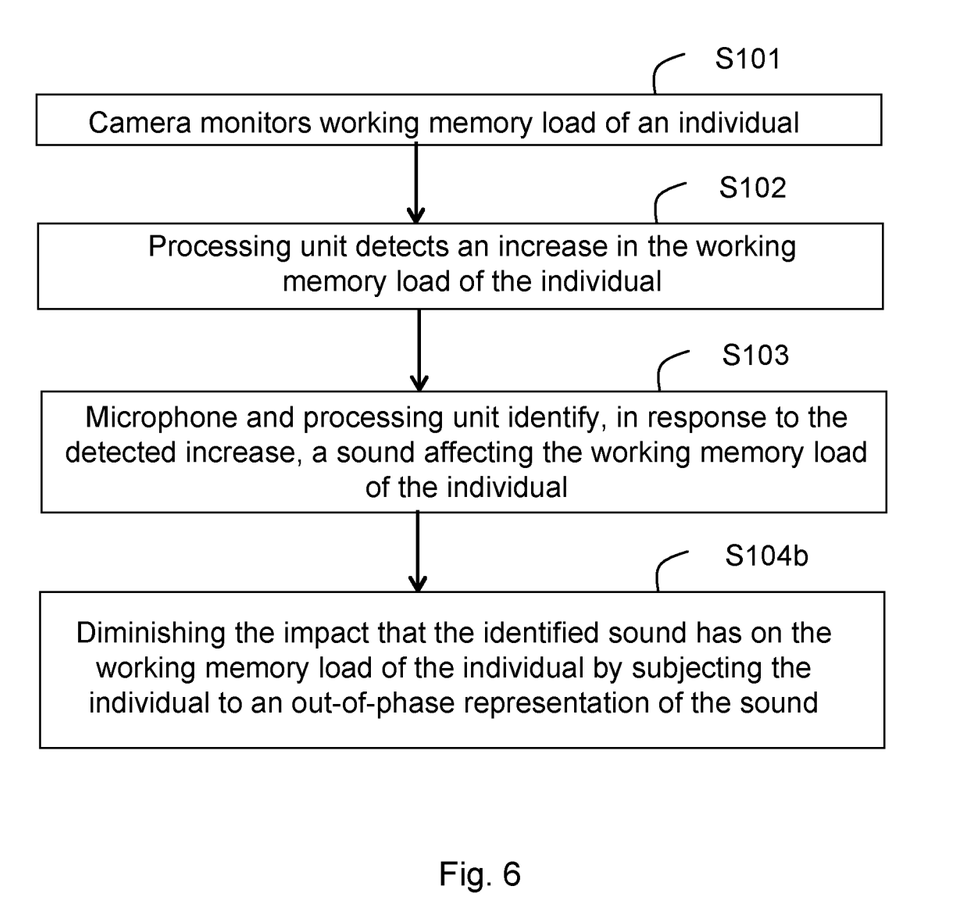
FIG. 6 illustrates a flowchart of a method of identifying sensory inputs affecting working memory load of an individual, according to yet another embodiment of the invention.

As can be seen in FIG. 5, the user 20 wears a pair of headphones 21 which in this example is equipped with noise-reducing capability. Now, the camera 12 of the computer 10 in cooperation with the processing unit 15 monitor and detect an increase in the working memory load of the user 20 in steps S101 and S102 as illustrated in FIG. 6, and a processing unit and microphone (not shown) of the headphones 21 serve as a sensory input detection device for registering disturbing background noise in step S103, as illustrated with the identified sound 22.

After receiving a wireless or wired signal 23 from the computer 10 indicating that an increase in working memory load has been detected in step S102, the processing unit of the noise-reducing headphones 21 advantageously initiates a countermeasure to the identified sensory input by subjecting the individual to a signal 24 which is an out-of-phase representation of the background noise 23 in step S104b, thereby effectively cancelling out the background noise.

In the above discussed embodiments, the camera 12 is used as a sensor device for monitoring and detecting an increase in working memory load of the user 20 in cooperation with the processing unit 15, by detecting changes in the pupil size of the user's eyes. It may further be envisaged that the camera 12 is used as a gaze detector with capability to track a direction of the user's visual attention and its duration.

Generally, people have a tendency to look at an object when using it for a task—someone working at a laptop will spend most of the task time looking at the laptop. Hence, if their gaze is suddenly shifted, this may be an indication that they have been distracted. When gaze is shifted to another object that is providing a sensory input (e.g., making a sound, displaying changing images, etc.), this may indicate that that object is causing distraction.

However, people may also shift gaze to concentrate, or for inspiration, such as looking skywards.

By tracking the user's gaze, and in particular recording the times she changes gaze from a device she is using for her task and toward an object providing a sensory input, a measurement can be made as to how often the user is likely being distracted. A signature 'inspiration' or 'concentration' gaze can be learnt for a given user and discounted from this measurement.

Further, it is envisaged that a worn device equipped with a camera is used as a sensor device for monitoring and detecting an increase in working memory load of the user in cooperation with a processing unit of the worn device, such as a virtual reality (VR) headset or a Google Glass type eyewear.

Moreover, activity tracking sensor devices that is able to identify specific activities the user is engaged in and possibly the user's efficiency in these activities is envisaged.

Similar to gaze, a person's motion can be used to assess the likelihood they are being distracted. Hence if the sensor device is a motion tracking sensor, and if the user shifts position often, particular in response to an object providing sensory input (e.g., a television) then the sensor's output can provide an indication that object is distracting. Therefore, by monitoring the person's motion, and if possible correlating this with objects in the room, then a measure can be made as to whether they are being distracted and by what.

An activity tracking sensor device may also track the progress of a task, for example number of words written in a document, increase in size of a file of a drawing file, number of cells adjusted in an Excel file etc.

Various sensor devices other than cameras can be envisaged, e.g., EEG sensors, EKG sensors, heart rate meters, etc.

Different properties may further be combined to detect an increase in the working memory load of the user, for instance by considering a combination of two or more of pupil size, gaze, heart rate, activity, EEG, etc.

Further, a number of types of devices for identifying sensory inputs affecting working memory load of an individual can be envisaged, such as laptops, tablets, smart phones, smart watches (using for instance heart rate as a measure of working memory load), television sets, etc.

In yet another embodiment, the user 20 is during a learning phase of the device 10 purposely subjected to different sensory inputs while changes in the working memory load of the individual are monitored. Further, a measure associated with each particular sensory input is estimated and stored in a database for subsequent use.

For instance, for any given user, a nominal working memory load may be recorded when the user practically is not subjected to any (disturbing) sensory input in her work environment. This lowest working memory load is denoted "$Load_{NOM}$", and corresponds to pupil size denoted "$PupilSize_{NOM}$".

Now, the user is subjected to different sensory inputs, and an increase in pupil size of the user's eyes is detected and a corresponding increase in working memory load, as will be illustrated in Table 1 herein below.

Hence, in an embodiment of the invention, a representation of any identified sensory input, and the corresponding measure with which said any identified sensory input affects the working memory load of the individual, is entered in a database as illustrated in Table 1.

Figure 7:
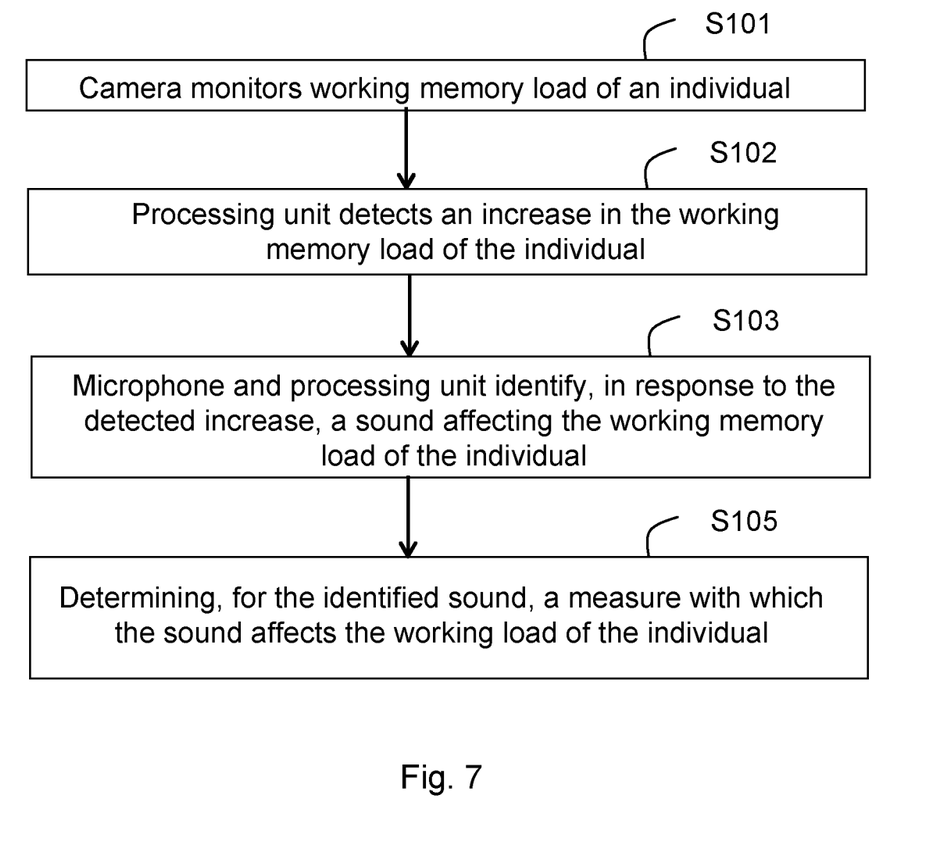
FIG. 7 illustrates a flowchart of a method of identifying sensory inputs affecting working memory load of an individual, according to a further embodiment of the invention.

Reference is further made to the flowchart of FIG. 7.

In a first round, the user 20 is subjected to three different sound levels of music selected from one of her playlists (i.e., music that the user indeed appreciates) and played through the loudspeaker 14 of her computer, while the camera 12 monitors the pupil size of the user's eyes in step S101 and the processing unit 15 detects a 0.1 mm increase, a 0.3 mm increase and a 0.5 mm increase, respectively, for the three (increasing) sound levels Sound level 1, Sound level 2, and Sound level 3, in step S102, which are considered in step S105 to correspond to a 10%, 30% and 50% increase in working memory load with respect to $Load_{NOM}$. The different sounds are identified by the microphone 13 and the processing unit 15 in step S103.

Hence, for each identified sensory input of the plurality of sensory inputs affecting the working memory load of the user 20, a measure with which each identified sensory input affects the working memory load of the user 20 is determined and entered in the database. This assessment is typically performed by the processing unit 15, but could alternatively be performed by the camera 12 itself. The three recorded sounds and their respective impact on the working memory load correspond to Items 1, 2, and 3, in Table 1.

In a second round, the user 20 is subjected to lighting conditions corresponding to indoor lighting of the office during a winterday. Again, the camera 12 monitors the pupil size of the user's eyes and the processing unit 15 detects a 0.2 mm increase, which is considered to correspond to a 20% increase in working memory load with respect to $Load_{NOM}$. This corresponds to Item 4 in Table 1.

In a third round, the user 20 is subjected to the sound of the office air conditioning system starting. The camera 12 monitors the pupil size of the user's eyes and the processing unit 15 detects a 0.1 mm increase, which is considered to correspond to a 10% increase in working memory load with respect to $Load_{NOM}$. This corresponds to Item 5 in Table 1.

TABLE 1

Recorded sensory inputs vs. increase in working memory load.

| Sensory input | Change in pupil size from nominal size | Increase in working memory load from nominal load |
|---|---|---|
| Sound level 1 of audio player | $PupilSize_{NOM}$ + 0.1 mm | $Load_{NOM}$ + 10% |
| Sound level 2 of audio player | $PupilSize_{NOM}$ + 0.3 mm | $Load_{NOM}$ + 30% |
| Sound level 3 of audio player | $PupilSize_{NOM}$ + 0.5 mm | $Load_{NOM}$ + 50% |
| Wintertime indoor lighting | $PupilSize_{NOM}$ + 0.2 mm | $Load_{NOM}$ + 20% |
| Air condition sound | $PupilSize_{NOM}$ + 0.1 mm | $Load_{NOM}$ + 10% |

Table 1 exemplifies five different items, while in a real-life scenario, tens of different sensory inputs may be recorded in order to cover an abundance of situations having potential to occur and thus increase the working memory load of the user.

It should be noted that a database such as that of Table 1 may be built with purposely subjecting the user 20 to sensory inputs, but can be built while the user 20 is "naturally" subjected to the sensory inputs. Further, the naturally occurring sensory inputs can be added to a database comprising sensory inputs to which the user 20 purposely has been subjected.

Figure 8:
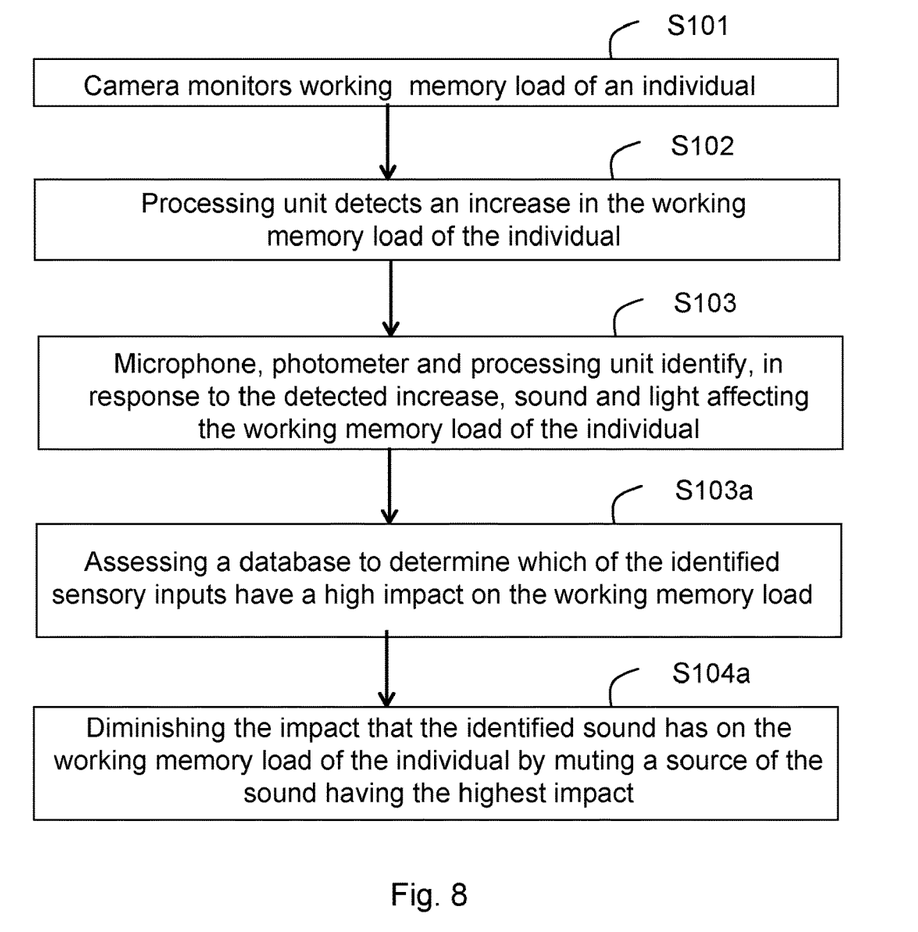
FIG. 8 illustrates a flowchart of a method of identifying sensory inputs affecting working memory load of an individual, according to yet a further embodiment of the invention.

In a further embodiment illustrated with reference to the flowchart of FIG. 8, the database of Table 1 is utilized to select which out of a number of sensory inputs that the user 20 is subjected to should be diminished to effectively decrease the working memory load of the user 20.

If an increase in working memory load of the user 20 is detected, some sensory inputs (i.e., sounds, visual inputs, and potentially even odours) may be removed or obscured in order to reduce the load on the user's working memory.

In other words—as distractions taking place within the locality of the user (i.e., within a distance that those activities can impact the senses of the user) provide sensory inputs that do not contribute to the execution of the user's task, the presence of these sensory inputs may be mitigated or even eliminated.

Assuming that that the user 20 of FIG. 2 is subjected to a plurality of sensory inputs, for instance those listed in Table 1, as identified by the microphone 13 as regards the audible sensory inputs and a photometer (not shown) identifying the indoor lighting in step S103 after an increase in load has been detected by the processing unit 15 in step S102. In such scenario, a problem which may arise is related to distinguishing which of the sensory inputs affects the user 20 the most.

By turning to the database of Table 1 in step S103a— assuming that the audio player of the computer 10 outputs music at Sound level 2—the processing unit 15 concludes that the audio player playing at Sound level 2 affects the user 20 as much as the indoor lighting and the sound of the air condition do jointly.

The processing unit 15 of the computer 10 may hence determine that the audio player is to be turned off in step S104a, or at least that its output sound level should be reduced, thereby advantageously decreasing the working memory load of the user 20.

Figure 9:
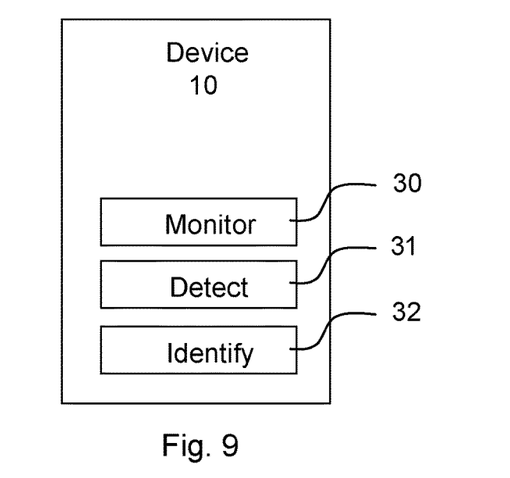
FIG. 9 illustrates a device for identifying sensory inputs affecting working memory load of an individual, according to another embodiment of the invention.

FIG. 9 illustrates a device 10 for identifying identify sensory inputs affecting working memory load of an individual. The device 10 comprises monitoring means 30 adapted to monitor working memory load of the individual, detecting means 31 adapted to detect an increase in the working memory load of the individual, and identifying means 32 adapted to identify, in response to detecting the increase, at least one sensory input affecting the working memory load of the individual.

The monitoring means 30, detecting means 31 and identifying means 32 may comprise communications interface(s) for receiving and providing information, and further a local storage for storing data, and may (in analogy with that previously discussed) be implemented by a processor embodied in the form of one or more microprocessors arranged to execute a computer program downloaded to a suitable storage medium associated with the microprocessor, such as a RAM, a Flash memory or a hard disk drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A device comprising:
processing circuitry, wherein the device is configured to:
monitor working memory load of an individual;
identify a first sensory input that is impacting the working memory load of the individual; and
after identifying the first sensory input, diminish the impact that the first sensory input has on the working memory load of the individual.

2. The device of claim 1, wherein identifying the first sensory input comprises detecting a sensory input coinciding in time with an increase in the working memory load of the individual.

3. The device of claim 1, wherein diminishing the impact that the first sensory input has on the working memory load of the individual comprises:
controlling a source of the first sensory input to diminish the impact that the first sensory input has on the working memory load of the individual.

4. The device of claim 1, wherein the diminishing the impact that the first sensory input has on the working memory load of the individual comprises:
initiating a countermeasure to the first sensory input to diminish the impact that the first sensory input has on the working memory load of the individual.

5. The device of claim 1, wherein identifying the first sensory input comprises:
identifying a plurality of sensory inputs; and
for each identified sensory input, determining a measure with which said identified sensory input is impacting the working memory load of the individual.

6. The device of claim 5, wherein the device is further configured to, based on said determined measure, determine the sensory input having the largest impact on the working memory load of the individual, wherein the sensory input determined to have the largest impact on the working memory load of the individual is the first sensory input.

7. The device of claim 5, wherein the device is further configured to:
store said measures in a database; and
use the stored measures to determine one or more high-impact sensory input types.

8. The device of claim 5, wherein identifying the first sensory input further comprises subjecting the individual to the plurality of sensory inputs.

9. The device of claim 5, wherein the plurality of sensory inputs comprises two or more of: an audible input, a visual input, a change in temperature, a change in humidity, or an odor.

10. The device of claim 1, wherein monitoring the working memory load of an individual comprises one or more of:
monitoring one or both eyes of the individual;
monitoring the individual's heartbeat; or
monitoring the individual's brain activity.

11. The device of claim 1, wherein the device is further configured to detect an increase in the working memory load of the individual.

12. The device of claim 11, wherein the identifying is performed as a result of detecting the increase in the working memory load of the individual.

13. The device of claim 11, wherein detecting the increase in the working memory load of the individual comprises detecting an increase in a pupil size.

14. The device of claim 1, wherein
the first sensory input is a noise, and
diminishing the impact that the first sensory input has on the working memory load of the individual comprises producing an out-of-phase representation of the noise.

15. The device of claim 1, wherein the device is further configured to:
identify a second sensory input that is impacting the working memory load of the individual; and after identifying the second sensory input, diminish the impact that the second sensory input has on the working memory load of the individual.

16. The device of claim 1, wherein the first sensory input is an audible input, a visual input, a change in temperature, a change in humidity, or an odor.

17. A method comprising:
monitoring working memory load of an individual;
identifying a first sensory input that is impacting the working memory load of the individual; and
after identifying the first sensory input, diminishing the impact that the first sensory input has on the working memory load of the individual.

18. The method of claim 17, wherein identifying the first sensory input comprises detecting a sensory input coinciding in time with an increase in the working memory load of the individual.

19. The method of claim 17, wherein diminishing the impact that the first sensory input has on the working memory load of the individual comprises:
controlling a source of the first sensory input to diminish the impact that the first sensory input has on the working memory load of the individual.

20. The method of claim 17, wherein the diminishing the impact that the first sensory input has on the working memory load of the individual comprises:
initiating a countermeasure to the first sensory input to diminish the impact that the first sensory input has on the working memory load of the individual.

21. The method of claim 17, wherein monitoring the working memory load of an individual comprises one or more of:
monitoring one or both eyes of the individual;
monitoring the individual's heartbeat; or
monitoring the individual's brain activity.

22. The method of claim 17, further comprising detecting an increase in the working memory load of the individual.

23. The method of claim 22, wherein the identifying is performed as a result of detecting the increase in the working memory load of the individual.

24. The method of claim 17, wherein
the first sensory input is a noise, and
diminishing the impact that the first sensory input has on the working memory load of the individual comprises producing an out-of-phase representation of the noise.

25. The method of claim 17, wherein the first sensory input is an audible input, a visual input, a change in temperature, a change in humidity, or an odor.

26. A non-transitory computer readable medium storing a computer program comprising computer-executable instructions which when executed by processing circuitry of a device causes the device to perform the method of claim 17.

* * * * *